United States Patent [19]
Murphy et al.

[11] Patent Number: 6,033,877
[45] Date of Patent: Mar. 7, 2000

[54] PEPTIDE EXPRESSION AND DELIVERY SYSTEM

[75] Inventors: Timothy F. Murphy, East Amherst, N.Y.; Kyungcheol Yi, Lilburn, Ga.

[73] Assignee: Research Foundation of State University of New York, Amherst, N.Y.

[21] Appl. No.: 08/740,644

[22] Filed: Oct. 31, 1996

Related U.S. Application Data

[60] Provisional application No. 60/006,168, Nov. 2, 1995.

[51] Int. Cl.[7] .......................... C12N 15/31; C12N 15/62; C12N 15/63; C12N 15/74
[52] U.S. Cl. ................. 435/69.7; 435/252.3; 435/320.1; 536/23.4; 530/350
[58] Field of Search .................... 435/69.1, 69.7, 435/91.1, 172.1, 172.3, 252.3, 252.33, 320.1, 471, 476, 477; 530/350, 403; 536/23.1, 23.4, 23.7

[56] References Cited

U.S. PATENT DOCUMENTS 5,348,867  9/1994  Georgiou et al. .................... 435/69.7

OTHER PUBLICATIONS

Haase et al. Mapping of Bacterial Epitopes on the P2 Porin Protein of Nontypable Haemophilus influenzae. Infect. Immun. 62: 3712–3722, Sep. 1994.

Davies, J. M, Molecular mimicry: Can epitope mimicry induce autoimmune disease? Immunol. Cell Biol. 75(2): 113–126, Apr. 1997.

Haase et al., "Mapping of Bactericidal Epitopes on the P2 Porin Protein of Nontypeable Haemophilus influenzae", Sep. 1994, vol. 62: 3712–3722.

Primary Examiner—David Guzo
Assistant Examiner—Thomas G. Larson
Attorney, Agent, or Firm—Hodgson, Russ, Andrews, Woods & Goodyear LLP

[57] ABSTRACT

This invention relates to methods and compositions for producing a fusion protein comprised of *Haemophilus influenzae* P2 amino acid sequences, wherein in place of loop 5, or a portion thereof, is displayed a heterologous or homologous peptide sequence having biological activity. The fusion protein may be expressed on the surface of the host cell, such as in *H. influenzae*, which has been transformed with a fusion sequence that is operatively linked to at least one regulatory control element for expression of the fusion protein. Alternatively, the fusion protein can be purified from the host cell in the expression system, if the fusion protein remains associated with the host cell; or from the media of the expression system, if the fusion protein is a secreted form.

38 Claims, 1 Drawing Sheet

PEPTIDE EXPRESSION AND DELIVERY SYSTEM

This application is a nonprovisional of my earlier provisional application U.S. Ser. No. 60/006,168, filed Nov. 2, 1996, which is herein incorporated by reference.

This invention was made with government support under grant AI19641 awarded by the National Institutes of Health. The government has certain rights in the invention.

FIELD OF THE INVENTION

The present invention relates to generally to the recombinant production of fusion proteins in host cells. More specifically, the invention relates to the expression by host cells of recombinant fusion sequences comprising sequences encoding *Haemophilus Influenzae* outer membrane protein P2, or a portion thereof, fused to sequences encoding one or more peptides, and the production and use of such fusion proteins, in isolated form or expressed at the surface of the host cell, to deliver peptides having biological activity.

BACKGROUND OF THE INVENTION

There are a variety of expression systems by which a protein or peptide can be recombinantly produced. Expression systems, wherein the protein or peptide is expressed and displayed as a part of the host cell surface, have applications including use as a peptide display library, as inactivated or live vaccines, and as antigens to generate antibodies. A protein or peptide, in a form isolated from an expression system, may be used as immunogens in vaccine formulations for active immunization; and can be used to generate protein-specific and peptide-specific antisera useful for passive immunization, and as reagents for diagnostic assays.

Expression of a peptide, in a recombinant host cell, has met with limited success. Frequently, peptides are poorly expressed in bacteria because intracellularly the peptide may encounter one or more difficulties including insolubility, instability, degradation, or sequestration. If a peptide is successfully recombinantly produced and purified, such isolated peptide may have reduced biological activity compared to the same amino acids which are part of the protein from which the peptide sequence is derived. Such reduced activity is typical because the active domain of the peptide is conformational rather than linear; and thus, in solution, the isolated peptide does not occur in proper conformation for full biological activity, or such proper conformation is only one of many alternative structures of the peptide.

To overcome the difficulties encountered in recombinant expression of peptides, there have been various attempts in the art to express a peptide in a conformation reflective of the conformation of the peptide when expressed as part of the protein from which it is derived. For example, one approach is to express the peptide as part of a fusion protein. Typically, a fusion protein consists of a microbial (e.g. bacterial) polypeptide backbone into which is incorporated an amino acid sequence representing one or more heterologous peptide sequences. A step in fusion protein expression comprises inserting into a gene, encoding the microbial polypeptide, a nucleic acid sequence encoding one or more heterologous peptides. Usually the gene is part of an expression vector, such that when the vector is introduced into a host cell system, the fusion protein is then produced either as remaining host cell-associated, or secreted into the culture medium of the expression system. Examples of microbial polypeptide backbone includes *Escherichia coli* proteins Lam B (Charbit et al., 1991, *J. Bacteriol.* 173:262–275), LacZ, trpE, maltose-binding protein, and thioredoxin (U.S. Pat. No. 5,292,646); a fusion protein including a portion of an *E. coil* or Salmonella lipoprotein with OmpA or Omp C or Omp F or Omp T (U.S. Pat. No. 5,348,867); bacterial flagellin (U.S. Pat. No. 4,801,536); *Schistosoma japonicum* glutathione-S-transferase; baculovirus polyhedrin (U.S. Pat. No. 4,745,051); and filamentous phage pIII (Scott and Smith, 1990, *Science* 249:386–390).

In the art of recombinant protein expression, there remains a need for new systems, and new compositions for the production and delivery of biologically active, stable peptides for use in diagnostic and therapeutic applications. One such need involves the delivery of biologically active, stable peptides to the respiratory tract for inducing mucosal immunity to one or more respiratory tract pathogens.

SUMMARY OF THE INVENTION

The present invention is directed to fusion proteins, in which peptides are expressed as a part thereof, using a polypeptide backbone comprising *H. influenzae* outer membrane protein P2 ("P2"). In one embodiment of the invention, into or replacing the portion of the P2 gene sequence encoding loop 5 of P2 is inserted a nucleic acid sequence encoding one or more peptides in forming a "fusion sequence". The fusion sequence may further comprise an additional nucleic acid sequence, located in frame but between the P2 gene sequence and the sequence encoding one or more peptides, which encodes an amino acid sequence having a function such as stabilizing the loop structure in the fusion protein, facilitating transport to the surface of the host cell and/or enabling secretion into the medium of the expression system. The fusion sequence, when incorporated into an expression vector and in operative association with a promoter, can then be expressed as a fusion protein upon introduction of the expression vector containing the fusion sequence into the host cell. Restriction sites already existing in the P2 gene within, or adjacent to, the loop 5 encoding region can be used to insert a nucleic acid sequence encoding one or more homologous or heterologous peptides. Alternatively, a restriction site already existing in the P2 gene within, or adjacent to, the loop 5 encoding region can be used to insert a polylinker containing additional restriction sites to facilitate the insertion of a nucleic acid sequence encoding one or more homologous or heterologous peptides into the loop 5 encoding region of the P2 gene.

In another embodiment, the fusion protein remains associated with the host cell. For example, the fusion protein is expressed in the outer membrane of *H. influenzae* in a manner similar to P2 expression in wild type *H. influenzae* isolates. Thus, the fusion protein displays one or more peptide sequences, incorporated into the P2 polypeptide backbone, in a loop 5 position which is surface-exposed relative to the bacterial outer membrane and the surrounding microenvironment. Recombinant *H. influenzae*, or mutants thereof, expressing the fusion protein and displaying surface-exposed peptide sequences, can be used to colonize the respiratory tract of individuals thereby immunizing by the mucosal route.

In another embodiment, the gene encoding P2 is altered such that a soluble form of P2 is produced. Accordingly, when the fusion sequence is incorporated into an expression vector, in operative association with a promoter, and the expression vector containing the fusion sequence is introduced into the host cell, a soluble form of the fusion protein is efficiently secreted into the culture medium of the expression system. Alternatively, using techniques known in the art for isolating proteins, particularly related to isolation of *H. influenzae* outer membrane proteins and to P2, host cell-associated fusion protein may be purified and isolated. The purified and isolated fusion proteins made according to the present invention may be used as immunogens in prophylactic and/or therapeutic vaccine formulations; or to generate specific antibody which may be useful for passive immunization or as reagents for diagnostic assays.

In an additional embodiment of the present invention, novel DNA sequences and vectors are constructed which can be used to direct the expression of fusion protein in appropriate host cells from which the expressed fusion protein may be purified.

DETAILED DESCRIPTION OF THE INVENTION

Definitions

Figure 2:
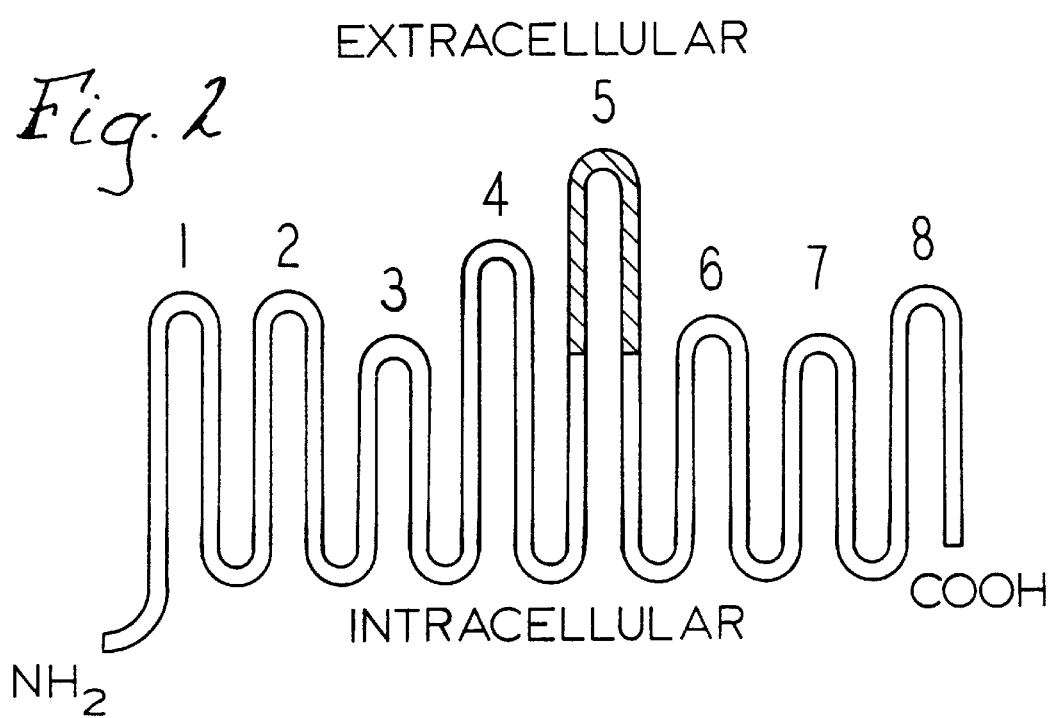
FIG. 2 is a schematic representation showing a topographical model of a fusion protein, when associated with *H. influenzae* outer membrane, using P2 as the polypeptide backbone.

"Fusion protein" is a term used hereinafter for the purposes of the specification and claims to refer to a modified *H. influenzae* outer membrane protein, P2, wherein at least one modification is the expression in or replacing of the loop 5 region of P2, amino acid sequences representing one or more peptides (See, e.g., FIG. 2).

"Fusion sequence" is a term used hereinafter for the purposes of the specification and claims to refer to a modified P2 gene wherein at least one modification is the insertion into, or replacing of, the portion of the P2 gene sequence encoding loop 5 of P2 with a nucleic acid sequence encoding one or more peptides. Additional modifications include, but are not limited to, at least one additional nucleic acid sequence, located in frame but between the P2 gene sequence and the sequence encoding one or more peptides, which: (a) encodes an amino acid sequence having a function including stabilizing the loop structure in the fusion protein, facilitating transport to the surface of the host cell and/or enabling secretion into the medium of the expression system, or a T-cell epitope; and/or (b) is a polylinker containing a plurality of restriction sites.

"Microbial pathogen" is a term used hereinafter for the purposes of the specification and claims to refer to a microorganism of a genus and species including, but not limited to, *Haemophilus influenzae, Branhamella catarrhalis, Bordetella pertussis*, Group A Streptococcus, *Streptococcus pnuemoniae, Pseudomonas aeruginosa, Legionella pneumophila, Mycoplasma pneumoniae*, Respiratory syncytial virus (RSV), Influenza virus, Adenovirus, rhinovirus, parainfluenza virus, and *Pneumocystis carinii.*

"Individual" is a term used hereinafter for the purposes of the specification and claims to refer to any mammal, especially humans.

"consisting essentially of", in relation to amino acid sequence of a protein or peptide, is a term used hereinafter for the purposes of the specification and claims to refer to a conservative substitution or modification of one or more amino acids in that sequence such that the tertiary configuration of the protein or peptide is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. "Modification", in relation to amino acid sequence of a protein or peptide, is defined functionally as a deletion of one or more amino acids which does not impart a change in the conformation, and hence the biological activity, of the protein or peptide sequence.

"consisting essentially of", in relation to a nucleic acid sequence, is a term used hereinafter for the purposes of the specification and claims to refer to substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the amino acid sequence encoded, are not expected to substantially alter the biological activity of the gene product. Thus, a nucleic acid sequencing encoding a protein or peptide as disclosed herein, may be modified slightly in sequence (e.g., substitution of a nucleotide in a triplet codon), and yet still encode its respective gene product of the same amino acid sequence.

*Haemophilus influenzae* is an important human respiratory tract pathogen in diseases including otitis media, chronic sinusitis, and chronic obstructive pulmonary disease. The P2 protein ("P2"), ranging in molecular size from about 36 to 42 kDa depending on the bacterial isolate, is the most abundant protein in the outer membrane of *H. influenzae* appearing to comprise approximately half of the protein content of the outer membrane. P2 is a porin which exists as a trimer and is closely associated with lipooligosaccharide in *H. influenzae.*

The presence of serum bactericidal antibody in children is associated with protection from infection by nontypeable *H. influenzae* (Faden et al., 1989, *J. Infect. Dis.* 160:999–1004). One of the specific targets of bactericidal antibody in human immune sera is P2 (Murphy et al., 1988, *Infect. Immun.* 56:2673–2679). Further, antibodies to P2 protect against infection resulting from *H. influenzae* type b in the infant rat model of experimental meningitis (Munson et al., 1983, *J. Clin. Invest.* 72:677–684). Using nine monoclonal antibodies (MAbs) to P2 having bactericidal activity, exclusively to the strain used to induce the respective MAb, it was demonstrated that eight of the nine MAbs recognized an epitope within residues 213 to 229 of loop 5 of P2 (Haase et al., 1994, *Infect. Immun.* 62:3712–3722; herein incorporated by reference).

The present invention is directed to methods of making a fusion protein which is expressed on the bacterial surface of *H. influenzae* and which can be used in a cell-associated form or purified and isolated before use; and a fusion protein which is secreted into the medium of the expression system, and thus can be purified and isolated in a soluble form. The present invention is also directed to fusion sequences comprising recombinant DNA for expressing a fusion protein stably anchored in the outer membrane of *H. influenzae* with peptide sequences displayed as a surface-exposed portion of the fusion protein; and fusion sequences comprising recombinant DNA for expressing a fusion protein loosely associated with the outer membrane of *H. influenzae*, or secreted in the medium of the expression system, wherein the fusion protein can be efficiently isolated and purified, with peptide sequences displayed as an outwardly-exposed portion in the conformation of the isolated and purified fusion protein. An expression system, comprising a recombinant vector for expressing the fusion sequence which is introduced into a host cell, can be used to produce fusion protein which can (a) be purified, or used in a whole cell form, for use as an immunogen in vaccine formulations; or (b) be used to produce peptide-specific antisera for passive immunization, or as reagents for diagnostic immunoassays.

For purposes of the description, but not limitation, the methods and compounds of the present invention are illustrated in the following examples.

EXAMPLE 1

The following example illustrates that the loop 5 portion of P2 contains an immunodominant epitope which induces antibody in immunized individuals.

Figure 1:
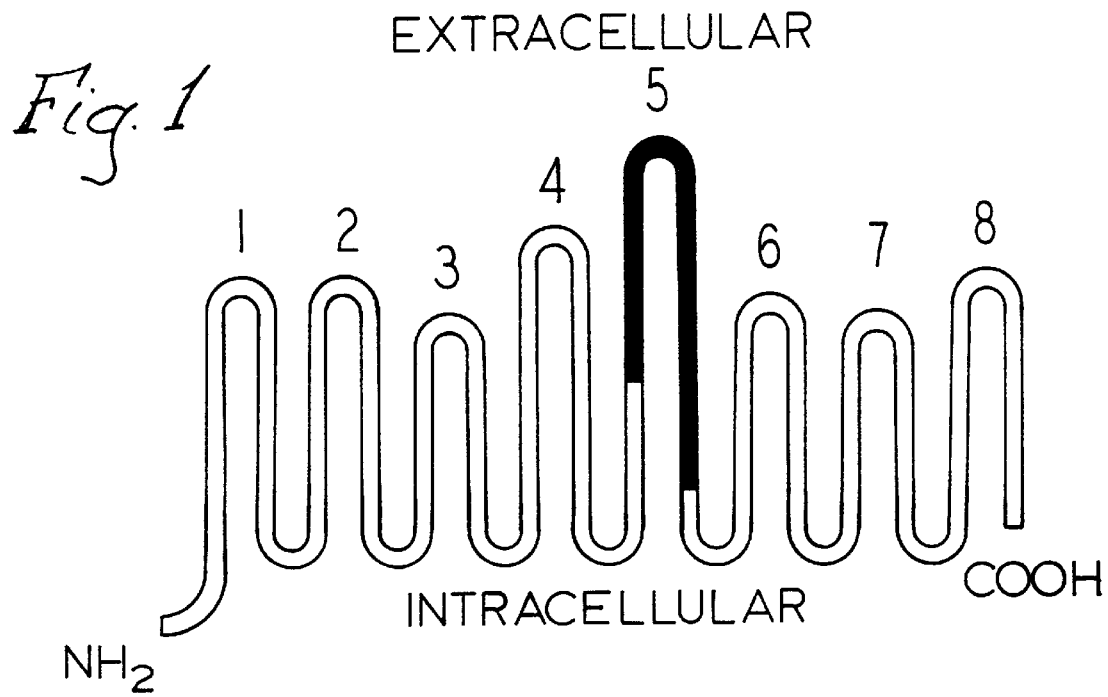
FIG. 1 is a schematic representation showing a topographical model of P2, when associated with *H. influenzae* outer membrane, containing 8 surface-exposed loops, and 16 transmembrane regions.

Immune sera to *H. influenzae* was raised by inoculating animals with whole bacterial cells of nontypeable *H. influenzae* strain 1479. Accordingly, five New Zealand white rabbits were immunized intravenously with approximately $2 \times 10^8$ bacteria on day 0 and with $1 \times 10^8$ bacteria on day 26. Also, five Balb/c mice were immunized intraperitoneally with approximately $7.5 \times 10^7$ bacteria on day 0 and with $5 \times 10^7$ bacteria on day 26. Antisera were collected on day 35. Analysis of the immune sera in immunoblot assay with a whole bacterial lysate of strain 1479 showed that the most prominent antibody response was directed to the P2 protein band. To analyze the regions of P2 to which immune sera antibodies were directed, the eight surface-exposed loops, according to the topographical model of P2 illustrated in FIG. 1, were individually expressed as fusion peptides with glutathione-S-transferase using the pGEX2T plasmid vector (See, e.g., Haase et al., 1994, supra).

With reference to SEQ ID NO:1, representing the P2 gene, primers were synthesized to enzymatically amplify the respective portion of the P2 gene which encodes the various loops (loop 1: amino acid (aa) 22–43; loop 2: aa 69–85; loop 3: aa 115–133; loop 4: aa 155–175; loop 5- aa 203–248; loop 6: aa 262–277; loop 7: aa 303–315; and loop 8: aa 331–364), with the primers being designed so that the amplified products had different restrictions sites to facilitate directional cloning. The pGEX-2T vector was digested with EcoRI and BamHI; the purified amplified products representing the various loop encoding sequences were also digested with EcoRI and BamHI; and digested vector was ligated using methods known in the art to each insert DNA by mixing digested vector with an insert DNA at a 1:2 molar ratio. Resultant recombinant vectors were introduced into *E. coli* strain DH5αF' by electroporation, and transformants were selected for antibiotic resistance, and screened for recombinant vectors of the expected size.

Fusion peptide was produced by growing a transformant in an overnight culture at 37° C. in 80 ml media supplemented with ampicillin. The overnight culture was diluted with fresh medium to 800 ml. After 1 hour of incubation at 37° C., isopropyl-β-D-thiogalactopyranoside (IPTG) was added to 0.4 mM; followed by 3–4 more hours of incubation. Cells were centrifuged at 10,000×g and the cell pellet was resuspended in 5 ml of PBS. Cells were sonicated and the mixture was centrifuged at 10,000×g for 10 minutes. The supernatant was mixed with 0.5 ml of pre-swelled glutathione-agarose beads. After mixing for 2 minutes at room temperature, the beads (with fusion peptide bound to the glutathione) were washed 2 additional times with buffer containing 1% detergent. The beads were then washed once in 0.05M Tris, pH 8.0. To elute the fusion peptide from the glutathione-S-transferase, the washed beads were mixed with and incubated in 5 mM reduced glutathione in Tris buffer for 1 hour at room temperature. The beads were removed by centrifugation and the supernatant contained purified fusion peptide.

The purified fusion peptides, each displaying one of the 8 loops of P2, were subjected to immunoblot assays with the various immune sera. All ten antisera showed a prominent antibody response exclusively to the loop 5 fusion peptide; i.e., all of the antibodies detected by immunoblot assay are directed to loop 5 only. To analyze whether the immune sera is directed to conformational epitopes not detectable by immunoblot assays, the loop 5 fusion peptide was used to adsorb the immune sera before the immune sera was tested by ELISA (with P2 purified under nondenaturing conditions) or radioimmunoprecipitation (RIP; using whole bacteria). Adsorption of aliquots of the 10 antisera with the loop 5 fusion peptide completely eliminated detectable reactivity between the antisera and P2 in ELISA. The loop 5 fusion peptide also adsorbed almost all antibody detected by RIP. These experiments confirm that all detectable P2 antibodies contained within the immune sera bind to epitopes present on loop 5.

Immunization with whole bacterial cells represents immunization with a complex array of antigens. However, the antisera resulting from such immunization is directed predominantly to P2. Further, most if not all of the antibody directed to P2 binds epitopes within the 46 amino acids comprising loop 5. The high degree of surface accessibility of loop 5 as related to P2 and *H. influenzae* bacterial cells is likely an important factor in it being recognized as immunodominant. As a region presenting epitopes that are recognized as immunodominant in an immune response, the P2 loop 5 region provides a structure particularly suitable for fusion with, and thereby display of, one or more heterologous or homologous peptide sequences. An additional advantage in using P2 loop 5 for displaying one or more peptide sequences is that P2 is amply expressed in *H. influenzae*; i.e., appears to comprise approximately half of the protein content of its outer membrane.

EXAMPLE 2

The following example illustrates the construction of recombinant DNA molecules containing fusion sequences.

To produce the fusion protein of the present invention, a host cell, preferably a strain of *H. influenzae*, is transformed with a vector containing, or has integrated into its genome, a recombinant DNA molecule comprising a modified P2 gene wherein at least one modification is the insertion into, or replacement of, the portion of the P2 gene sequence encoding loop 5 of P2 with a nucleic acid sequence encoding one or more selected peptides, and wherein the modified P2 gene is operatively linked to a expression control sequence capable of directing the expression of the fusion protein. One skilled in the art would appreciate that for the fusion protein to be produced, any modifications of the P2 gene would require that the nucleic acid sequence(s) be joined in frame with the P2 gene sequences to allow for expression of the resultant recombinant DNA molecule.

The nucleotide sequence of the P2 gene, and the deduced amino acid sequence of its gene product P2, used to illustrate the present invention are shown in SEQ ID NO:1. A comparison of the deduced amino acid sequences, from genes encoding outer membrane protein P2 isolated from various strains, indicates that P2 varies in amino acid composition amongst strains (Sikkema and Murphy, 1992, *Infect. Immun.* 60:5204–5211; Dium et al. 1993, *Microbial Path.* 14:451–462; and Bell et al., 1994, 62:2639–2643; all herein incorporated by reference). The variable regions, in both the P2 gene sequences and amino acid sequences, appear to occur primarily within the surface-exposed loops of P2. Sequence conservation appears in the membrane spanning segments of P2 (Sikkema and Murphy, 1992, supra; Dium et al., 1993, supra). As a biological consequence of such sequence variability in the surface-exposed loops of P2, antibodies generated to P2 elicited during infection are usually strain-specific, and therefore subsequent protection is solely strain-specific. Analysis of the sequence of loop 5, containing the immunodominant epitope of P2, from 13 P2 genes from nontypeable *H. influenzae* show significant sequence heterogeneity. This observation indicates that loop 5 represents a site "permissive" of substantial sequence heterogeneity, while still maintaining a P2 protein having stable biological activity. Thus, as a "permissive" site, the P2 loop 5 region provides a structure particularly suitable for fusion with, and thereby display of, one or more heterologous or homologous peptide sequences.

In one embodiment of the present invention, an isolated nucleotide sequence consisting essentially of a P2 gene is modified by restriction enzyme digestion to remove all or a portion of the sequence encoding loop 5. It will be recognized by those skilled in the art that the P2 gene could be isolated from any strain of *H. influenzae*, that the choice and position of restriction enzyme sites within the region of the P2 gene encoding loop 5 may vary depending on the particular strain from which the gene is isolated, and that restriction enzymes are easily identifiable using the available computer programs for sequence analysis.

Essentially, one or more restriction enzymes unique to and selected from the sequence of the region of the P2 gene encoding loop 5, as compared to the remainder of the P2 gene, is utilized for an insertion site into which is inserted and ligated a nucleotide sequence encoding one or more peptides. In the process of restriction and ligation, and depending on the size of the sequence to be inserted, either all or a portion of the sequence encoding loop 5 is removed, or additional sequence is added. The nucleotide sequence to be inserted, need have ends compatible with the ends of the restricted P2 gene in order to facilitate ligation. In another variation, of this embodiment, into the restricted P2 is inserted a polylinker sequence having a plurality of restriction enzyme sites to facilitate the cloning of a nucleotide sequence encoding one or more peptides. Alternatively, the P2 gene and the nucleotide sequence to be inserted each can be cut so that each has blunt ends, which can then be blunt end-ligated together.

As a specific example of this embodiment, the P2 gene isolated from strain 1479 (SEQ ID NO:1) is restricted with RsaI (at nucleotide position 666 in SEQ ID NO:1) and BsaHI (at nucleotide position 728 in SEQ ID NO:1). Such restriction would remove the portion of the nucleotide sequence encoding amino acids 222 to 243 of P2 (loop 5 is approximately amino acids 203–248). Alternatively, the P2 gene isolated from strain 1479 (SEQ ID NO:1) can be restricted with RsaI and HgaI (at nucleotide position 736 in SEQ ID NO:1). Such restriction would remove the portion of the nucleotide sequence encoding amino acids 222 to 246 of P2. A sequence encoding a peptide comprising an antigen of a microbial pathogen, either having compatible ends or blunt ends, is then ligated to the P2 arms resulting from restriction of the P2 gene, with methods known to those skilled in the art and keeping in mind that the sequence is ligated in frame with the P2 arms.

In a related embodiment, two arms of the P2 gene can be synthesized to exclude all or a portion thereof of the sequence encoding loop 5. The 5' half of the strain 1479 P2 gene is amplified by polymerase chain reaction (PCR) using a forward primer (SEQ ID NO:2), and a reverse primer (SEQ ID NO:3). The 3' half of the P2 gene is amplified by polymerase chain reaction (PCR) using a forward primer (SEQ ID NO:4), and a reverse primer (SEQ ID NO:5) DNA containing the P2 gene sequences may be amplified using any one of several protocols for amplifying nucleic acids by the polymerase chain reaction. In one mode of this embodiment, the P2 gene sequences were amplified using the following conditions. DNA to be amplified (≈1 μg of genomic DNA) was distributed in 0.5 ml microfuge tubes and the volume was adjusted to 50 μl by adding a reaction mixture comprising 0.2 mM dNTPs (DATP, dCTP, dGTP, dTTP), 0.25 μg of each positive and negative oligonucleotide primer, 1 unit of TaqI polymerase, TaqI 10×buffer (5 μl), 1 mM $MgCl_2$ (final concentration), and sterile distilled water to achieve the total volume. The TaqI polymerase is added to the reaction mixture just before use and is gently mixed, not vortexed. A layer of mineral oil, approximately 2 drops, is added to each tube and then the tubes are placed in the thermal cycler. Thirty to thirty-five cycles are generally sufficient for bacterial DNA amplification. One cycle consists of 1 minute at 95° C., 1 minute at 37° C., and 1 minute at 72° C. The first cycle includes a 1½ minute incubation at 95° C. to assure complete denaturation. After separation of the amplified DNA on 1% agarose gel, the 5' and 3' fragments are cloned into a vector. As a result, three restriction sites (HindIII, SacII, and KpnI) can be used as a site for directional cloning of a sequence encoding a vaccine antigen of a microbial pathogen. The resultant recombinant vector, if an expression vector, can then be introduced into an appropriate host cell system for expression. If the resultant recombinant vector is just for purposes of construction of the fusion sequence, the fusion sequence may then be moved into an expression vector.

Additional modifications, in the construction of recombinant DNA molecules containing fusion sequences, may include the insertion of least one additional nucleic acid sequence, located in frame but between the P2 gene sequence and the sequence encoding one or more peptides, which has a functional purpose other than providing a plurality of restriction sites for facilitating cloning. Such a nucleic acid sequence may encodes an amino acid sequence of sufficient length serving as a linker; i.e., having a function of stabilizing the loop structure in the fusion protein, and/or preventing steric hinderances between the P2 portion, and the peptide portion of the fusion protein, by reducing the conformational freedom of the peptide portion and thereby reducing the possible number of alternative structures. As known to those skilled in the art, the linker-encoding sequence may or may not be a necessary part of the fusion sequence depending upon the structural characteristics of the peptide(s) to be displayed as part of the fusion protein.

In a related embodiment, and where secretion of the fusion peptide is desired, such an additional nucleic acid sequence included as part of the fusion sequence may encode a secretory leader. Various secretory leaders are known in the art and include, but are not limited to, leader sequences of chondroitin ABC lyase, *B. pertussis* S1, phoa, MBP, and fl-lactamase. Incorporation of a secretory leader sequence in the fusion protein may enable expression and secretion of the fusion protein through the outer membrane of the *H. influenzae* host, and into the culture medium for subsequent purification. Alternatively, genetic engineering techniques (e.g., by site-directed mutagenesis) may also be used to modify fusion in a sequence in the P2 gene, other than that encoding the loop 5 domain of P2, such as in at least one transmembrane region encoding sequence, to increase the solubility of the encoded fusion protein to allow for easier purification.

In another related embodiment, such an additional nucleic acid sequence included as part of the fusion sequence may encode a peptide comprising a T-cell epitope. T-cells play a major role as helper cells for efficient antibody production. A T-cell epitope promotes specific helper T-cell responses in generating a efficient and effective immune response, and can overcome genetic restrictions in an immune response to an antigen, thereby broadening the effective response in a large number of genetically diverse individuals. Particularly desirable if the isolated fusion protein is to be used in a vaccine, a peptide consisting of a T-cell epitope may result in an enhanced immune response compared to a fusion protein lacking the T-cell epitope. T-cell epitopes having defined sequences which can be incorporated into a fusion protein, as understood by those skilled in the art, include, "promiscuous" T-cell epitopes from tetanus toxin (Panina-Bordignon et al., 1989, *Eur. J. Immunol.* 19:2237–2242; Ho et al., 1990, *Eur. J. Immunol.* 20:477; Kaumaya et al., 1993, *J. Mol. Recognition,* 6:81–94; all herein incorporated by reference); and from measles virus (Partidos and Stewart, 1990, *J. Gen. Virol.* 71, 2099–2105; herein incorporated by reference); and "universal" T-cell epitope peptides (T2, T4, and T6) from bacterial outer membrane protein TraT (Russell-Jones, 1993, *Vaccine* 11:1310, herein incorporated by reference).

EXAMPLE 3

The following example illustrates the insertion of recombinant DNA molecules (with fusion sequences) into vectors.

As will be discussed in more detail below, *H. influenzae* has a natural genetic transformation process involving linearized DNA binding, uptake via one or more uptake sequences (e.g. AAGTGCGGT-SEQ ID NO:6), translocation, and recombination. Thus, one mechanism to introduce a recombinant DNA molecule containing the fusion sequence to be expressed into the fusion protein, is to transform the host *H. influenzae* with linearized recombinant DNA molecule containing the fusion sequence. Alternatively, the recombinant DNA molecule containing the fusion sequence to be expressed can be inserted into a plasmid vector, and either introduced into as a linearized recombinant molecule by the natural transformation process; as circularized recombinant plasmid using electroporation of noncompetent *H. influenzae*; or as a circularized recombinant plasmid transformed into competent *H. influenzae*.

Plasmids useful for cloning of and expression from recombinant DNA molecules in *H. influenzae* are known to those skilled in the art. Such plasmids include:

pRSF0885 confers ampicillin resistance, and contains a PvuII cloning site and a defective TnA sequence (Setlow et al., 1981, *J. Bacteriol.* 148:804–811), and can replicate in both *H. influenzae* and *E. coli* (Trieu et al., 1990, *Gene* 86:99–102).

pDM2 was constructed by cloning chloramphenicol resistance into pRSF0885; and pDM5 was constructed by cloning tetracycline resistance into pRSF0885 (McCarthy et al., 1986, *J. Bacteriol.* 168:186–191).

pVT63, pVT64, pVT65, pVT66 are improved shuttle vectors for *H. influenzae* and *E. coil* based on pDM2 (Trieu et al., 1990, *Gene* 86:99–102), and contain the pUC-derivative of the ColE1 ori, and the pRSF0885 rep locus. Additionally, each plasmid has drug markers with unique restriction sites for insertional inactivation of the drug marker as follows: pVT63- ApR (HincII, PstI, ScaI), KmR (ClaI, HindIII, NruI, SmaI, XhoI); pVT64- ApR (HincII, PstI, ScaI, SspI), SpR; pVT65- ApR (HincII, PstI, ScaI, PvuI, SspI), CmR (BalI, NcoI); pVT66- ApR (HincII, PstI, ScaI, PvuI) , CmR (SmaI) .

pACYC177, pACYC184, pSU2718, pSU2719 are improved shuttle vectors for *H. influenzae* and *E. coli* based on p15A (Chandler, 1991, *Plasmid* 25:221–224), have the p15A ori, and were compatible with a plasmid containing the RSF0885 origin of replication. Additionally, each plasmid has multiple cloning sites restriction sites and drug markers as follows: pACYC177- ApR, KmR (Accession No. X06402); pACYC184- CmR, TcR (Accession No. X06403); pSU2718- CmR and polycloning site from pUC18 (Accession No. M64731); and pSU2719- CmR and polycloning site from pUC19 (Accession No.M64732).

pQL1 is an improved shuttle vector for use in *H. influenzae* and *E. coli* containing both the pMB1 ori and P15a ori, KmR which is flanked by *H. influenzae* uptake sequences, a multiple cloning site containing a unique BamHI and SmaI restriction sites, and which is particularly suited for analyzing *H. influenzae* promoter strength in *H. influenzae* (Heidecker et al., 1994, *Gene* 150:141–144).

In cloning the recombinant DNA molecule containing the fusion sequence, with or without an additional nucleic acid sequence, into a plasmid vector, one skilled in the art will appreciate that the choice of restriction enzymes for digesting both the recombinant DNA molecule and the plasmid to result in compatible ends for ligation depends on the unique restriction enzyme sites at the ends of the recombinant DNA molecule, whether occurring naturally or engineered such as during enzymatic amplification; one or more unique restriction enzyme sites within the plasmid vector; whether insertion into the plasmid vector will assist in the selection process (See, e.g., pVT66); and whether a plasmid-derived promoter is used solely, or in addition to the P2 promoter, to drive expression from the recombinant DNA molecule. Selection and screening of transformed *H. influenzae* may be accomplished by methods known in the art including detecting the expression of a marker gene (e.g., drug resistance marker) present in the plasmid, and immunodetection of the expressed and displayed heterologous peptide sequence.

While this embodiment illustrates that the recombinant DNA molecule containing the fusion sequence can be inserted into a plasmid and expressed in *H. influenzae*, it will be appreciated by those skilled in the art that vectors other than plasmids, and other expression systems can be used including, but not limited to, bacteria transformed with a bacteriophage vector, or cosmid DNA; yeast containing yeast vectors; fungi containing fungal vectors; insect cell lines infected with virus (e.g. baculo-virus—See, e.g., U.S. Pat. No. 4,745,051); and mammalian cell lines transfected with plasmid or viral expression vectors, or infected with recombinant virus (e.g. vaccinia virus, adenovirus, adeno-associated virus, retrovirus, etc.).

Successful expression of the fusion protein requires that either the recombinant DNA molecule comprising the fusion sequence, or the vector itself, contain the necessary control elements for transcription and translation which is compatible with, and recognized by the particular host system used for expression. Using methods known in the art of molecular biology, including methods described above, various promoters and enhancers can be incorporated into the vector or the recombinant DNA molecule containing the fusion sequence to increase the expression of the fusion protein, provided that the increased expression of the fusion protein is compatible with (for example, non-toxic to) the particular host cell system used. The fusion sequence can contain DNA encoding more than one peptide antigen selected from bacterial, fungal, parasitic, or viral antigens to create a multivalent antigen for use as an improved vaccine composition.

The selection of the promoter will depend on the expression system used. For example, a preferred promoter in an *H. influenzae* expression system is the P2 promoter operatively linked to the fusion sequence. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted fusion sequence encoding the fusion peptide.

Additionally, the fusion protein may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus, expression of the fusion protein may be controlled by culturing transformed or transfected cells under conditions such that the promoter controlling the expression from the fusion sequence encoding the fusion protein is not induced, and when the cells reach a suitable density in the growth medium, the promoter can be induced for expression from the inserted DNA. For example, P2 expression has been reported to be toxic to *E. coli* transformants. However, using pET vectors, and controlling the synthesis of recombinant P2 prior to induction of expression, subsequent induction can result in the production of P2 in *E. coli*, wherein P2 is sequestered into inclusion bodies (Pullen et al., 1995, *Gene* 152:85–88).

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the fusion sequence encoding the fusion protein to increase transcriptional efficiency. Other specific regulatory sequences may be identified in association with the P2 gene, and may play a role in expression from the P2 gene. These or other regulatory sites, such as transcription or translation initiation signals, can be used to regulate the expression of the fusion sequence. Such regulatory elements may be inserted into the recombinant DNA molecule containing the fusion sequence, or nearby vector DNA sequences using recombinant DNA methods described herein, and known to those skilled in the art, for insertion of DNA sequences.

Accordingly, a recombinant DNA molecule containing a fusion sequence, can be ligated into an expression vector at a specific site in relation to the vector's promoter, control, and regulatory elements so that when the recombinant vector is introduced into the host cell, the fusion sequence (with or without an additional nucleic acid sequence encoding a linker, T cell epitope, secretory leader, or a combination thereof) can be expressed in the host cell. For example, the fusion sequence containing its own (P2) regulatory elements can be ligated into an bacterial expression vector in a relation or orientation to the vector promoter, and control elements which will allow for expression of the fusion protein. The recombinant vector is then introduced into the appropriate bacterial host cells, and the host cells are selected, and screened for those cells containing the recombinant vector. Selection and screening may be accomplished by methods known in the art, and depending on the vector and expression system used.

EXAMPLE 4

The following example illustrates the introduction of recombinant DNA molecules (with fusion sequences), or vectors containing the same, into *H. influenzae*.

Expression of the fusion protein in *H. influenzae* is one preferred embodiment of the present invention. The introduction of a recombinant DNA molecule containing the fusion sequence (including an expression vector or plasmid containing the same) into *H. influenzae* can be accomplished in any one of three processes: a natural genetic transformation process; transformation of competent bacterial cells; and electroporation of non-competent bacterial cells.

Natural Transformation Process

The natural genetic transformation process of *H. influenzae* involves linearized DNA binding, uptake via one or more uptake sequences, translocation, and recombination. Thus, one mechanism to introduce a recombinant DNA molecule containing the fusion sequence to be expressed into the fusion protein, is to transform the host *H. influenzae* with linearized recombinant DNA molecule containing the fusion sequence; or a linearized vector having inserted into it the recombinant DNA molecule containing the fusion sequence to be expressed. In this natural process, when the linearized DNA is translocated intracellularly, one of the translocated strands of DNA is apparently degraded by exonuclease activity (Barany et al., 1983, *Proc. Natl. Acad. Sci. USA* 80:7274–7278). If the translocated strand lacks homology sufficient for recombination into the *H. influenzae* chromosome, the translocated strand becomes susceptible to further degradation (Pifer et al., 1985, *Proc. Natl. Acad. Sci. USA* 82:3731–3735). Using methods known in the art (e.g., Barany et al., 1983, supra), linearized DNA containing the fusion sequence can be introduced into *H. influenzae*. Since the fusion sequence contains P2 sequences, particularly conserved sequences which flank the loop 5 encoding region or sequences encoding one or more peptides inserted therein, recombination of the fusion sequence into the *H. influenzae* genome is likely to occur. Recombination of P2 gene sequences into the *H. influenzae* genome appears to occur in the natural transformation process. For example, horizontal transfer of DNA and recombination of P2 gene sequences is thought by some to cause the diversity in the P2 gene observed in nontypeable *H. influenzae* (Duim et al., 1993, supra; Porras et al., 1986, *Infect. Immun.* 53:79–89).

Transformation of Competent Bacterial Cells

Another mechanism to introduce a recombinant DNA molecule containing the fusion sequence to be expressed into the fusion protein, is to transform competent host *H. influenzae* with a circular vector, such as a plasmid, having inserted into it the recombinant DNA molecule containing the fusion sequence to be expressed. Competence of *H. influenzae* develops best under conditions in which the bacterial cell duplication is inhibited, such as a temporary shift to anaerobic conditions, by physiological change occurring during late-log phase growth, and transfer of cells into nutrient-poor, chemically-defined medium Such defined media for the development of competence of *H. influenzae* has been previously described in detail (Herriott et al., 1970, *J. Bacteriol.* 101:517–524. Briefly, competent *H. influenzae* can be prepared by resuspending bacterial cells (e.g., 5×10$^8$ to 5×10$^9$ cells), and incubating (e.g., 35 ml with rotation for 70 to 100 minutes) in media M-IV. Media M-IV contains 4,032 μg/ml L-aspartic acid, 314 μg/ml L-glutamic acid, 21 μg/ml L-arginine, 12 μg/ml L-citrulline, 2.5 μg/ml glycine, 35 μg/ml L-lysine, 18 μg/ml L-methionine, 65 μg/ml L-serine, 61 μg/ml L-leucine, 42 μg/ml L-tyrosine, 13 μg/ml L-histidine, 6 μg/ml L-cystine, 46 μg/ml L-phenylalanine, 20 μg/ml L-threonine, 33 μg/ml L-isoleucine, 35 μg/ml L-valine, 48 μg/ml L-alanine, 50 μg/ml L-proline, 1,000 μg/ml fumaric acid, 200 μg/ml detergent (TWEEN 20), 0.08M NaCl, 5×10$^{-4}$M MgSO$_4$, 0.00M CaCl$_2$, and 0.01M KH$_2$PO$_4$-K$_2$HPO$_4$. For transformation, less than one DNA molecule per competent cell (e.g., 50 ng DNA to 2 ml of 3×10$^9$ to 4.6×10$^9$ cells) is added, and incubated at 37° C., followed by termination of transformation at 0° C. It appears that only a short time after entering competent *H. influenzae*, a plasmid containing sequences homologous to the bacterial chromosome can insert its homologous sequence (such as the fusion sequence) into the chromosome via recombination (Setlow et al., 1981, supra). for expression. Thus, in this embodiment, a plasmid containing the fusion sequence (with or without an additional nucleic acid sequence encoding a linker, T cell epitope, secretory leader, or a combination thereof) which is capable of being transformed into competent *H. influenzae* is introduced by methods for transformation known in the art (Karudapuram et al., 1995, *J. Bacteriol.* 177:3235–3240; Setlow et al., 1981, supra. The fusion sequence is then recombined into the *H. influenzae* genome where it is expressed under the control of its own promoter or an *H. influenzae* promoter near the site of insertion. Such transformation is reported to be at a relatively high frequency (McCarthy and Cox, 1986, *J. Bacteriol.*, 168:186–191).

Alternatively, transformation of competent *H. influenzae* by a circular plasmid with the appropriate origin(s) of replication and containing the fusion sequence (with or without an additional nucleic acid sequence encoding a linker, T cell epitope, secretory leader, or a combination thereof) may result in plasmid establishment; i.e., a plasmid coexisting as an extrachromosomal element without recombination. Examples of such plasmids have been described above. Thus, in this variation of the embodiment, a plasmid containing the fusion sequence (with or without an additional nucleic acid sequence encoding a linker, T cell epitope, secretory leader, or a combination thereof) which is capable of being transformed into, and established in, competent *H. influenzae* is introduced by methods for transformation known in the art. The fusion sequence is then expressed from the plasmid under the control of its own promoter or a promoter within the vector.

Electroporation of Non-Competent Bacterial Cells

Yet another mechanism to introduce a recombinant DNA molecule containing the fusion sequence to be expressed into the fusion protein, is to introduce a circular vector, such as a plasmid having inserted into it the recombinant DNA molecule containing the fusion sequence to be expressed, into non-competent host *H. influenzae* by electroporation. Electroporation has been used to efficiently introduce plasmid DNA into bacteria. However, optimal conditions may differ depending on the host cell used. Optimal conditions have been described for electroporating plasmid DNA into *H. influenzae* (Mitchell et al., 1991, *Nucl. Acids Res.* 19:3625–3628. Briefly, competent *H. influenzae* cells are ice-chilled for 30 min, harvested by centrifugation at 4200× g, and washed five times with phosphate-glycerol (PSG) buffer (15% glycerol, 272 mM sucrose, 2.43 mM K$_2$HPO$_4$, 0.57 mM KH$_2$PO$_4$, pH 7.2) at 4° C. The washes are centrifuged at 4200×g for 20 minutes. The last pellet is drained and suspended in PSG buffer to provide a concentration of OD$_{650}$ of 12 for a 1 cm path. DNA (0.1 to 1.0 ug, in 1–4 ul in water) is added to the ice-chilled cells, stored on ice for 1 min, and transferred to cuvettes and subjected to electroporation in a commercially available apparatus at 2.5 kV, 400 ohms and 25 μF. It was found that electroporation of plasmid into *H. influenzae* made competent by defined, nutrient poor media was several orders of magnitude less efficient than electroporation into non-competent *H. influenzae*. Thus, in this variation of the embodiment, it would be preferred that a plasmid containing the fusion sequence (with or without an additional nucleic acid sequence encoding a linker, T cell epitope, secretory leader, or a combination thereof) is electroporated into non-competent *H. influenzae*. The plasmid is capable of being established in *H. influenzae*, or is degraded after the fusion sequence has recombined into the *H. influenzae* genome. In either case, the fusion sequence is under the control of its own promoter; or a promoter within the vector or genome, respectively.

EXAMPLE 5

The following example illustrates the various compositions of fusion proteins.

In accordance with the methods and materials illustrated in Example 2, a fusion sequence can be constructed which is then inserted into an expression system for expression into a fusion protein. As a "permissive" site, the P2 loop 5 region (SEQ ID NO:7) provides a structure particularly suitable for fusion with, and thereby display of, one or more heterologous or homologous peptide sequences. Thus, a nucleotide sequence consisting essentially of a P2 gene is modified by restriction enzyme digestion to remove all (SEQ ID NO:8) or a portion of the sequence encoding loop 5, and ligated in its place is a nucleotide sequence encoding one or more heterologous or homologous peptide sequences. An illustration of portions of loop 5 that can be deleted and replaced with peptide sequences, includes P2 amino acids 203–248; P2 amino acids 203–232; P2 amino acids 213–229; P2 amino acids 222–243; and P2 amino acids 222–246 (amino acid numbering as from SEQ ID NO:1).

While modification of the complete P2 gene is a preferred embodiment in generating a fusion sequence, one of skill in the art will appreciate that only a portion of the P2 gene sequence is needed. It can be determined from a fusion protein, produced from a fusion sequence containing a portion of the P2 gene, whether it contains the peptide sequences displayed as a loop that is structurally and functionally equivalent to the loop 5 region of P2 by comparing its three dimensional structure by one or more methods including monoclonal antibody surface mapping (if the fusion protein is expressed as a membrane protein), x-ray crystallography, or NMR spectroscopy.

According to the present invention, the fusion protein comprises a left arm and a right arm of P2 amino acid sequences, with one or more peptide sequences inbetween at a location in the P2 protein that comprises all or part of the loop 5 region. An antigenic site (an epitope) may vary in size but can consist of from about 7 to about 14 amino acids. Thus, the peptide sequence portion of the fusion protein can comprise one or more epitopes. Accordingly, the peptide sequence portion of the fusion protein can comprise of at least 7 amino acids, and as many as 50 amino acids or more, provided that the peptide sequence is displayed as a loop in the fusion protein. As provided in Example 2, a linker can be incorporated into the fusion protein for the purpose of stabilizing the fusion protein such that a loop structure is formed in which the peptide sequence is displayed.

In one embodiment of the present invention, the peptide sequences displayed in the fusion protein comprise one or more peptides which antigenically mimic epitopes from microbial pathogens. In a preferred embodiment, a microbial pathogen may include a respiratory pathogen selected from the group of pathogens, with respective antigens, in Table 1.

TABLE 1

| PATHOGEN | INFECTION | PROTEIN ANTIGEN |
|---|---|---|
| *H. influenzae* | otitis media, lower respiratory tract | D-15, P1, P6[1] |
| Group A Streptococcus | pharyngitis, rheumatic fever | M[2] |
| *Branhamella catarrhalis* | otitis media, lower respiratory tract | CD, E[3] |
| *Streptococcus pneumoniae* | pneumonia, otitis media, meningitis | autolysin, pneumolysin[4] |
| *Bordetella pertussis* | pertussis (whooping cough) | filamentous hemagglutinin, pertussis toxin, 69kDa Omp[5] |
| *Pseudomonas aeruginosa* | respiratory tract | Omp OprF, exotoxin A[6] |
| *Legionella pneumophila* | pneumonia | OmpS, Hsp60[7] |
| *Mycoplasma pneumoniae* | upper and lower respiratory tract | P1[8] |
| Respiratory syncytial virus | lower respiratory tract | M2, P, F, G[9] |
| Influenza virus | influenza | HA, M[10] |
| Adenovirus | common cold | |
| rhinovirus | common cold | VP1, VP2, VP3[11] |
| Parainfluenza virus | common cold | HN, F[12] |
| *Pneumocystis carinii* | pneumonia in AIDS | msg[13] |

[1](Flack et al., 1995 Gene 156:97–99; Panezutti et al., 1993, 61:1867–1872; Nelson et al., 1988, Rev Infect Diseases 10:S331–336).
[2](Pruksakorn et al., 1994, Lancet 344:639–642; Dole et al., 1993, J Immunol 151:2188–94).
[3](Murphy et al., 1989, Infect Immun 57:2938–2941; Faden et al., 1992, Infect Immun 60:3824–3829).
[4](Lock et al., 1992, Microb Pathog 12:137–143).
[5](Novotny et al., 1991, Dev Biol Stand 73:243–249; Lipscombe et al., 1991, Mol Microbiol 5:1385–1392; He et al., 1993, Eur J Clin Microbiol Infect Dis 12:690–695).
[6](Rawling et al., 1995, Infect Immun 63:38–42; Pennington et al., 1988, J Hosp Infect 11A:96–102).
[7](Weeratna et al., 1994, Infect Immun 62:3454–3462).
[8](Jacobs et al., 1990, Infect Immun 58:2464–2469; 1990, J Clin Microbiol 28:1194–1197).
[9](Kulkarni et al., 1995, J Virol 69:1261–1264; Leonov et al., 1994, J Gen Virol 75:1353–1359; Garcia et al., 1993, Virology 195:239–242; Vaux-Peretz et al., 1992, Vaccine 10:113–118).
[10](Kaly et al., 1994, Vaccine 12:753–760; Bucher et al., 1980, J Virol 36:586–590).
[11](Francis et al., 1987, J Gen Virol 68:2687–2691).
[12](Morein et al., 1983, J Gen Virol 64:1557–1569).
[13](Garbe et al., 1994, Infect Immun 62:3092–3101).

Table 1, and the references footnoted which are herein incorporated by reference, illustrate various protein antigens, or peptides thereof, thought to be useful in a vaccine against the respective microbial pathogen. Typically, the immunopotency of an epitope, whether from a protein or peptide, of a microbial pathogen is determined by monitoring the immune response of an animal following immunization with the epitope and/or by analyzing human convalescent sera in conjunction with pre-immune sera. Thus, one skilled in the art can determine protein or peptide antigens from microbial pathogens which would be desired to include as the peptide sequence to be displayed in the fusion protein according to the present invention. A corresponding nucleic acid sequence for encoding the peptide sequence can then be deduced from the amino acid sequence of the protein or peptide, wherein that nucleic acid sequence is incorporated as part of the fusion sequence for expression of a fusion protein.

In another embodiment, rather than representing an epitope of a microbial pathogen, the peptide sequence displayed as part of the fusion protein may represent a biologically active peptide to be delivered in vivo. Such a biologically active peptide can be selected from a nonimmunogenic molecule selected from a hormone, drug, cytokine, growth factor, inhibitory factor, or enzyme. A large number of nonimmunogenic, biologically active molecules, and their encoding nucleic acid sequences, are known to those skilled in the art.

EXAMPLE 6

The following example illustrates methods of using the fusion protein in diagnostic immunoassays.

Fusion protein can be purified for use as immunogens in vaccine formulations against disease caused by *H. influenzae* and/or by the pathogen from which is derived the peptide antigen portion (amino acid sequences other than P2 amino acid sequences) displayed as part of the fusion protein. Also, the purified fusion protein can be used as an immunogen for generating specific antisera, recognizing the peptide antigen portion displayed as part of the fusion protein, for therapeutic and/or diagnostic value. Such antisera may include polyclonal antisera, since the loop 5 region of P2, or the peptide displayed therein, represents an immunodominant antigen.

The fusion protein produced from an expression vector system, can be purified with methods known in the art including detergent extraction, chromatography (e.g., ion exchange, affinity, immunoaffinity, or sizing columns), differential centrifugation, differential solubility, or other standard techniques for the purification of proteins. For example, the purification of P2 protein from *H. influenzae* has been described previously (Murphy and Bartos, 1988, *Infect. Immun.* 56:1084–1089). Thus, the fusion protein, expressed in *H. influenzae*, can be isolated from *H. influenzae* via the majority portion being P2 amino acid sequences. Essentially, *H. influenzae* cultures from 30 chocolate agar plates are scraped into 25 ml of PBS, pH 7.2, and harvested by centrifugation at 12,000×g for 20 minutes at 4° C. The bacterial pellet is then resuspended in 10 ml of 1 M sodium acetate-0.001 M β-mercaptoethanol (pH 4.0). A 90-ml volume of a solution containing 5% Zwittergent Z 3–14 (Calbiochem-Behring) and 0.5% M $CaCl_2$ is added, and the suspension is mixed for 1 hour at room temperature. Nucleic acids are precipitated by the addition of cold ethanol to 20%, and subsequent centrifugation at 17,000×g for 10 minutes at 4° C. The remaining proteins are precipitated by the addition of cold ethanol to 80% and collected by centrifugation at 17,000×g for 20 minutes at 4° C. The pellets are allowed to dry and then are suspended in 10 ml of detergent buffer containing 0.05% zwitterionic detergent, 0.05 M Tris, 0.01 M EDTA, pH 8.0, and mixed for 1 hour at room temperature. The bacterial outer membrane proteins, including the fusion protein, and some lipooligosaccharide (LOS) are present in the soluble fraction of the detergent buffer after centrifugation at 12,000×g for 10 minutes at 4° C. The fusion protein, like P2, may be further purified from other outer membrane proteins by anion-exchange chromatography using a column equilibrated with zwitterionic detergent buffer and using a linear elution gradient of 0 to 2 M NaCl in the buffer, and collection of fractions as monitored by optical density at a wavelength of 280 nm and by polyacrylamide gel electrophoresis of collected fractions. The fusion protein, like P2, may be separated from LOS using additional anion-exchange chromatography. Fractions containing the fusion protein and LOS are precipitated with ethanol and dissolved in a sodium deoxycholate detergent buffer containing 0.05 M Tris, 0.15 M NaCl, 1.5% sodium deoxycholate, pH 9.0. The pH is then adjusted to 11 with 1 N NaOH and stirred. Insoluble material is then removed by centrifugation. The supernatant is applied to an anion exchange column and eluted using the sodium deoxycholate buffer. Fractions containing the fusion protein are collected separately from those containing LOS.

Immunopurification of the fusion protein from an outer membrane protein preparation, or a host cell, or medium of the host cell expression system, may be accomplished using methods known in the art for immunoaffinity chromatography. P2-specific monoclonal antibodies (such as 5F2 recognizing loop 8 of P2; Haase et al., 1994, supra) may be linked to a chromatographic matrix to form an affinity matrix. The protein preparation, from which the fusion protein is to be isolated and purified, is then incubated with the affinity matrix allowing the antibodies to bind to the P2 portion. The affinity matrix is then washed to remove unbound components and the fusion protein is then eluted from the affinity matrix resulting in a purified preparation of fusion protein. The purified fusion protein may be used as an antigen for generating antibodies (against the peptide antigen portion displayed by the fusion protein) useful as reagents in immunodiagnostic assays including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

EXAMPLE 7

The following example illustrates methods of using the fusion protein in vaccine preparations.

This embodiment of the present invention is to provide fusion protein to be used in as immunogens in a prophylactic and/or therapeutic vaccine for active immunization to protect against or treat infections caused by microbial pathogens. For vaccine purposes, the peptide sequence displayed as part of the fusion protein represents an antigen that is immunogenic, and induces functional antibodies directed to one or more surface-exposed epitopes on the respective microbial pathogen wherein the epitope(s) are conserved amongst strains of the respective microbial pathogen.

For vaccine development, the fusion protein may be purified from transformed H. influenzae or may be purified from a host containing a recombinant vector which expresses fusion protein. Such hosts include, but are not limited to, bacterial transformants, yeast transformants, filamentous fungal transformants, and cultured cells that have been either infected or transfected with a vector containing the fusion sequence which encodes the fusion protein. The fusion protein is then included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. For example, respiratory immunity can be stimulated by intestinal immunization with purified H. influenzae antigens (Cripps et al., 1992, J. Infect Dis 165S1:S199–201; herein incorporated by reference).

The vaccine may further comprise a physiological carrier such as a solution, a polymer or liposomes; and an adjuvant, or a combination thereof. Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc.

Another mode of this embodiment provides for either a live recombinant viral vaccine, recombinant bacterial vaccine, recombinant attenuated bacterial vaccine, or an inactivated recombinant viral vaccine which is used to protect against infections caused by microbial pathogen. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as the peptide antigen(s) displayed as part of the fusion protein, thereby providing long-lasting immunity.

Other live vaccine vectors include: adenovirus, cytomegalovirus, and preferably the poxviruses such as vaccinia (Paoletti and Panicali, U.S. Pat. No. 4,603,112; herein incorporated by reference). Live bacterial vaccine vectors attenuated Salmonella strains (Stocker et al., U.S. Pat. Nos. 5,210,035; 4,837,151; and 4,735,801; and Curtiss et al., 1988, Vaccine 6:155–160; herein incorporated by reference), Shigella flexneri (Sizemore et al., 1995, Science 270:299–302; herein incorporated by reference), and transformed H. influenzae. As mentioned herein, one preferred embodiment is to provide a vaccine delivery system for human respiratory tract pathogens. Thus, immunization by the parental route or by the mucosal route with H. influenzae, transformed to express the fusion protein, can lead to colonization of the respiratory tract to induce mucosal immunity against the displayed peptide antigen(s) portion of the fusion protein. Live vaccines are particularly advantageous because they continually stimulate the immune system which can confer substantially long-lasting immunity. When the immune response is protective against subsequent H. influenzae infection, the live vaccine itself may be used in a preventative vaccine against H. influenzae.

To illustrate this mode of the embodiment, using molecular biological techniques such as those illustrated in Example 2, the fusion sequence may be inserted into the vaccinia virus genomic DNA at a site which allows for expression of the fusion protein but does not negatively affect the growth or replication of the vaccinia virus vector. The resultant recombinant virus can be used as the vector in a vaccine formulation which expresses the peptide antigen (s).

Similar methods can be used to construct an inactivated recombinant vaccine formulation except that the recombinant virus or bacterial host is inactivated, such as by chemical means known in the art, prior to use as an immunogen and without substantially affecting the immunogenicity of the expressed immunogen. For example, human bronchial mucosal immunity has been stimulated with an aerosol vaccine comprising lysed *H. influenzae* (Latil et al., 1986, *J Clin Microbiol* 23:1015–1021). The inactivated recombinant vaccine may also be formulated with a suitable adjuvant in order to enhance the immunological response to the peptide antigen(s) expressed by the vaccine vector.

In another variation of this embodiment, genetic material is used directly as the vaccine formulation. Nucleic acid (DNA or RNA) containing a fusion sequence, operatively linked to one or more regulatory elements can be introduced directly to vaccinate the individual ("direct gene transfer") against the respective microbial pathogen upon subsequent expression of the fusion protein displaying one or more peptide antigens mimicking an epitope(s) of that pathogen. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, Science 261:209–211; herein incorporated by reference). Additionally, the recombinant DNA of the present invention may further comprise one or more immunostimulatory DNA sequences known to be necessary for optimal immunization (Sato et al., 1996, *Science* 273:352).

Other effective methods for delivering vector DNA into a target cell are known in the art. In one example, purified recombinant plasmid DNA containing viral genes has been used to inoculate (whether parentally, mucosally, or via gene-gun immunization) vaccinees to induce a protective immune response (Fynan et al., 1993, Proc. Natl. Acad. Sci. USA 90:11478–11482; herein incorporated by reference). One preferred method of vaccination with genetic material comprises the step of administering to the individual the nucleic acid molecule that comprises a fusion sequence that encodes for a fusion protein, wherein the fusion sequence is operatively linked to one or more regulatory sequences necessary for expression. The nucleic acid molecule can be administered directly, or first introduced into a vector and administered via the recombinant vector. The nucleic acid molecule can be administered in a pharmaceutically acceptable carrier or diluent and may contain compounds that can enhance the effectiveness of the vaccine. These additional compounds include, but are not limited to, adjuvants that enhance the immune response, and compounds that are directed to modulate the immune response, e.g. cytokines, collectively referred to as "immune modulators"; or other compounds which increase the uptake of nucleic acid by the cells, referred to as "nucleic acid uptake enhancers". The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express the fusion protein.

As an alternative to active immunization, such as where an immunocompromised individual is suffering from a potentially life-threatening infection, immunization may be passive, i.e. immunization comprising administration of purified human immunoglobulin containing antibody against the peptide antigen(s) displayed as part of the fusion protein.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

We claim:

1. A recombinant DNA molecule comprising in frame for expression, a first nucleotide sequence encoding *Haemophilus influenza* P2 protein, and a second nucleotide sequence encoding one or more peptides from a microbial pathogen, wherein the first nucleotide sequence has inserted therein, in place of a nucleic acid sequence encoding all or a portion of loop 5 amino acids, the second nucleotide sequence.

2. The recombinant DNA molecule according to claim 1, further comprising at least one additional nucleic acid sequence, located in frame between the first nucleotide sequence and the second nucleotide sequence, wherein said nucleic acid sequence has a function selected from the group consisting of encoding a peptide which stabilizes the loop structure in a fusion protein encoded by the recombinant DNA molecule, encoding a peptide which facilitates transport of a fusion protein encoded by the recombinant DNA molecule to the surface of a host cell containing and expressing the recombinant DNA molecule, encoding a peptide which enables secretion into the medium of a fusion protein encoded by the recombinant DNA molecule expressed in a host cell containing the recombinant DNA molecule, encoding a T-cell epitope, comprising a polylinker containing at least one restriction site, and a combination thereof.

3. A recombinant vector comprising the recombinant DNA molecule according to claim 1.

4. A recombinant vector comprising the recombinant DNA molecule according to claim 1 operatively linked to one or more regulatory elements.

5. A recombinant vector comprising the recombinant molecule according to claim 2.

6. A recombinant vector comprising the recombinant molecule according to claim 2 operatively linked to one or more regulatory elements.

7. The recombinant vector according to claim 3, further comprising an uptake sequence for transformation of *Haemophilus influenzae.*

8. The recombinant vector according to claim 4, further comprising an uptake sequence for transformation of *Haemophilus influenzae.*

9. The recombinant vector according to claim 5, further comprising an uptake sequence for transformation of *Haemophilus influenzae.*

10. The recombinant vector according to claim 6, further comprising an uptake sequence for transformation of *Haemophilus influenzae.*

11. A host cell containing the recombinant DNA molecule according to claim 1.

12. The host cell according to claim 11, wherein the host cell is a strain of *H. influenzae.*

13. A host cell containing the recombinant DNA molecule according to claim 2.

14. The host cell according to claim 13, wherein the host cell is a strain of *H. influenzae.*

15. A host cell containing the recombinant vector according to claim 3.

16. The host cell according to claim 15, wherein the host cell is a strain of *H. influenzae.*

17. A host cell containing the recombinant vector according to claim 4.

18. The host cell according to claim 17, wherein the host cell is a strain of *H. influenzae.*

19. A host cell containing the recombinant vector according to claim 5.

20. The host cell according to claim 19, wherein the host cell is a strain of *H. influenzae.*

21. A host cell containing the recombinant vector according to claim 6.

22. The host cell according to claim 21, wherein the host cell is a strain of *H. influenzae.*

23. A host cell containing the recombinant vector according to claim 7.

24. The host cell according to claim 23, wherein the host cell is a strain of *H. influenzae.*

25. A host cell containing the recombinant vector according to claim 8.

26. The host cell according to claim 25, wherein the host cell is a strain of *H. influenzae.*

27. A host cell containing the recombinant vector according to claim 9.

28. The host cell according to claim 27, wherein the host cell is a strain of *H. influenzae.*

29. A host cell containing the recombinant vector according to claim 10.

30. The host cell according to claim 29, wherein the host cell is a strain of *H. influenzae.*

31. A fusion protein encoded by the recombinant DNA molecule according to claim 1.

32. A fusion protein encoded by the recombinant DNA molecule according to claim 2.

33. A method of making a fusion protein comprising introducing the recombinant DNA molecule according to claim 1 into a host cell, wherein the host cell containing the recombinant DNA molecule expresses the fusion protein when grown under suitable conditions.

34. A method of making a fusion protein comprising introducing the recombinant DNA molecule according to claim 2 into a host cell, wherein the host cell containing the recombinant DNA molecule expresses the fusion protein when grown under suitable conditions.

35. A method of making a fusion protein comprising introducing the recombinant DNA molecule according to claim 3 into a host cell, wherein the host cell containing the recombinant DNA molecule expresses the fusion protein when grown under suitable conditions.

36. A method of making a fusion protein comprising introducing the recombinant DNA molecule according to claim 4 into a host cell, wherein the host cell containing the recombinant DNA molecule expresses the fusion protein when grown under suitable conditions.

37. A method of making a fusion protein comprising introducing the recombinant DNA molecule according to claim 5 into a host cell, wherein the host cell containing the recombinant DNA molecule expresses the fusion protein when grown under suitable conditions.

38. A method of making a fusion protein comprising introducing the recombinant DNA molecule according to claim 6 into a host cell, wherein the host cell containing the recombinant DNA molecule expresses the fusion protein when grown under suitable conditions.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1173 nucleotides
      (B) TYPE: nucleic acid
      (C) STRANDEDNESS: double-stranded
      (D) TOPOLOGY: linear (ii) MOLECULE TYPE: genomic DNA (iii) HYPOTHETICAL: yes (iv) ORIGINAL SOURCE:
      (A) ORGANISM: H. influenzae
      (B) STRAIN: 1479
      (C) CELL TYPE: bacterium (v) SEQUENCE DESCRIPTION: SEQ ID NO:1:

```
ATG AAA AAA ACA CTT GCA GCA TTA ATC GTT GTT GCA TTC GCA GCT          45
Met Lys Lys Thr Leu Ala Ala Leu Ile Val Val Ala Phe Ala Ala
 1               5                  10                  15

TCA GCA GCA AAC GCA GCT GTT GTT TAT AAC AAC GAA GGG ACT AAA          90
Ser Ala Ala Asn Ala Ala Val Val Tyr Asn Asn Glu Gly Thr Lys
                20                  25                  30

GTA GAA TTA GGC GGT CGT TTA AGC GTT ATT GCG GAA CAA AGC AGC         135
Val Glu Leu Gly Gly Arg Leu Ser Val Ile Ala Glu Gln Ser Ser
                35                  40                  45

AGC ACT GAA GAT AAT CAA GAA CAG CAA CAC GGT GCA TTA CGT AAT         180
Ser Thr Glu Asp Asn Gln Glu Gln Gln His Gly Ala Leu Arg Asn
                50                  55                  60

CAG GGT TCA CGT TTC CAC ATT AAA GCA ACG CAT AAC TTC GGT GAT         225
Gln Gly Ser Arg Phe His Ile Lys Ala Thr His Asn Phe Gly Asp
                65                  70                  75

GGT TTC TAT GCA CAA GGT TAT TTA GAA ACT CGT TTT GTT TCA AAA         270
Gly Phe Tyr Ala Gln Gly Tyr Leu Glu Thr Arg Phe Val Ser Lys
                80                  85                  90

GCC TCT AAA GAA AAA GCA GAT CAA TTC GCT GAT ATT GTA AAC AAA         315
Ala Ser Lys Glu Lys Ala Asp Gln Phe Ala Asp Ile Val Asn Lys
                95                 100                 105

TAT GCT TAT CTT ACT TTA GGA AAT AAC ACA TTC GGT GAA GTA AAA         360
Tyr Ala Tyr Leu Thr Leu Gly Asn Asn Thr Phe Gly Glu Val Lys
               110                 115                 120

CTT GGT CGC GCA AAA ACT ATT GCT GAT GAA ATT ACA ACC GCA GAA         405
Leu Gly Arg Ala Lys Thr Ile Ala Asp Glu Ile Thr Thr Ala Glu
               125                 130                 135

GAT AAA GAA TAT GGT CTT CTC AAC TCT AAA AAA TAT ATC CCT ACT         450
Asp Lys Glu Tyr Gly Leu Leu Asn Ser Lys Lys Tyr Ile Pro Thr
               140                 145                 150

AAT GGT AAC ACC GTT GGC TAT ACT TTT AAT GGT ATT GAT GGT TTA         495
Asn Gly Asn Thr Val Gly Tyr Thr Phe Asn Gly Ile Asp Gly Leu
               155                 160                 165

GTA TTA GGC GCT AAT TAT TTA TTA GCA CAA GAG CGT GAT TTA CGG         540
Val Leu Gly Ala Asn Tyr Leu Leu Ala Gln Glu Arg Asp Leu Arg
               170                 175                 180

ACT CTT GAT TCT AGA ACT AAT CCT ACG AAA AGT GGT GAA GTA ACT         585
Thr Leu Asp Ser Arg Thr Asn Pro Thr Lys Ser Gly Glu Val Thr
               185                 190                 195

GTA GGT GAA GTC AGT AAC GGA ATT CAA GTT GGT GCA AAA TAT GAT         630
Val Gly Glu Val Ser Asn Gly Ile Gln Val Gly Ala Lys Tyr Asp
               200                 205                 210

GCT AAC AAC ATT ATT GTA GCT ATT GCT TAC GGT CGT ACA AAT TAT         675
Ala Asn Asn Ile Ile Val Ala Ile Ala Tyr Gly Arg Thr Asn Tyr
               215                 220                 225

AAA GAC AGT AAT CAT AGT TAT ACG CAA AAA ATC CCC AAA GCC AAC         720
Lys Asp Ser Asn His Ser Tyr Thr Gln Lys Ile Pro Lys Ala Asn
               230                 235                 240

GCC GCC GAC GCC GAC ACC GAC ACC ACC ATA ATT TAC CCC CAT CAC         765
Ala Ala Asp Ala Asp Thr Asp Thr Thr Ile Ile Tyr Pro His His
               245                 250                 255

GGT AAA AAA CAA GAA GTA AAT GGT GCT TTA GCT AGT TTA GGT TAC         810
Gly Lys Lys Gln Glu Val Asn Gly Ala Leu Ala Ser Leu Gly Tyr
               260                 265                 270

CGT TTT AGT GAT TTA GGC TTA TTA GTC TCT CTA GAT AGT GGC TAT         855
Arg Phe Ser Asp Leu Gly Leu Leu Val Ser Leu Asp Ser Gly Tyr
               275                 280                 285
```

```
GCA AAA ACT AAA AAC TAT AAA GCT AAA CAC GAA AAA AGC TAT TTC              900
Ala Lys Thr Lys Asn Tyr Lys Ala Lys His Glu Lys Ser Tyr Phe
                290                 295                 300

GTA TCT CCA GGT TTC CAA TAT GAA TTA ATG GAA GAT ACT AAT GTC              945
Val Ser Pro Gly Phe Gln Tyr Glu Leu Met Glu Asp Thr Asn Val
                305                 310                 315

TAT GGC AAC TTC AAA TAT GAA CGT AAT TCA GTA GAT CAA GGT GAG              990
Tyr Gly Asn Phe Lys Tyr Glu Arg Asn Ser Val Asp Gln Gly Glu
                320                 325                 330

AAA GAA CGT GAA CAA GCA CTG TTA TTC GGT ATA GAT CAT AAA CTT             1035
Lys Glu Arg Glu Gln Ala Leu Leu Phe Gly Ile Asp His Lys Leu
                335                 340                 345

CAC AAA CAA GTA TTA ACC TAT ATT GAA GGT GCT TAC TCT AGA ACT             1080
His Lys Gln Val Leu Thr Tyr Ile Glu Gly Ala Tyr Ser Arg Thr
                350                 355                 360

AGA ACA ACT TCT GTA GGT GAT AAG CAA GTT GCT TCA AAA GTA AAA             1125
Arg Thr Thr Ser Val Gly Asp Lys Gln Val Ala Ser Lys Val Lys
                365                 370                 375

ACT GAA AAA GAA AAA TCA GTG GGT GTA GGT TTA CGC GTT TAC TTC             1170
Thr Glu Lys Glu Lys Ser Val Gly Val Gly Leu Arg Val Tyr Phe
TAA 1173
```

(2) INFORMATION FOR SEQ ID NO:2:

(i) SEQUENCE CHARACTERISTICS:
        (A) LENGTH: 34 nucleotides
        (B) TYPE: nucleic acid
        (C) STRANDEDNESS: single-stranded
        (D) TOPOLOGY: linear (ii) ORIGINAL SOURCE:
        (A) ORGANISM: H. influenzae
        (B) STRAIN: 1479

(iii) IMMEDIATE SOURCE: synthesized (iv) SEQUENCE DESCRIPTION: SEQ ID NO:2:

GCGTGTCGAC GCTGTTGTTT ATAACAACGA AGGG                                     34

(2) INFORMATION FOR SEQ ID NO:3:

(i) SEQUENCE CHARACTERISTICS:
        (A) LENGTH: 58 nucleotides
        (B) TYPE: nucleic acid
        (C) STRANDEDNESS: single-stranded
        (D) TOPOLOGY: linear (ii) ORIGINAL SOURCE:
        (A) ORGANISM: H. influenzae
        (B) STRAIN: 1479

(iii) IMMEDIATE SOURCE: synthesized (iv) SEQUENCE DESCRIPTION: SEQ ID NO:3:

GCTTCCGCGG GGTACCATAA TTTGTACGAC CGTAAGCAAT AGCTACAATA                    50

ATGTTGTT                                                                  58

(2) INFORMATION FOR SEQ ID NO:4:

(i) SEQUENCE CHARACTERISTICS:
        (A) LENGTH: 58 nucleotides
        (B) TYPE: nucleic acid
        (C) STRANDEDNESS: single-stranded
        (D) TOPOLOGY: linear (ii) ORIGINAL SOURCE:
             (A) ORGANISM: H. influenzae
             (B) STRAIN: 1479

(iii) IMMEDIATE SOURCE: synthesized (iv) SEQUENCE DESCRIPTION: SEQ ID NO:4:

TACCCCGCGG AAGCTTAAAA AACAAGAAGT AAATGGTGCT TTAACTAGTT                50

TAGGTTAC                                                              58

(2) INFORMATION FOR SEQ ID NO:5:

(i) SEQUENCE CHARACTERISTICS:
             (A) LENGTH: 39 nucleotides
             (B) TYPE: nucleic acid
             (C) STRANDEDNESS: single-stranded
             (D) TOPOLOGY: linear (ii) ORIGINAL SOURCE:
             (A) ORGANISM: H. influenzae
             (B) STRAIN: 1479

(iii) IMMEDIATE SOURCE: synthesized (iv) SEQUENCE DESCRIPTION: SEQ ID NO:5:

CGATGCGGCC GCTTAGAAGT AAACGCGTAA ACCTACACC                             39

(2) INFORMATION FOR SEQ ID NO:6:

(i) SEQUENCE CHARACTERISTICS:
             (A) LENGTH: 9 nucleotides
             (B) TYPE: nucleic acid
             (C) STRANDEDNESS: single-stranded
             (D) TOPOLOGY: linear (ii) ORIGINAL SOURCE:
             (A) ORGANISM: H. influenzae (iii) FEATURE:
             (A) OTHER INFORMATION: uptake sequence for transformation (iv) SEQUENCE DESCRIPTION: SEQ ID NO:6:

AAGTGCGGT                                                              9

(2) INFORMATION FOR SEQ ID NO:7:

(i) SEQUENCE CHARACTERISTICS:
             (A) LENGTH: 46 amino acid residues
             (B) TYPE: amino acid
             (C) TOPOLOGY: linear (ii) MOLECULE TYPE:
             (A) DESCRIPTION: protein (iii) ORIGINAL SOURCE:
             (A) ORGANISM: H. influenzae (iv) SEQUENCE DESCRIPTION: SEQ ID NO:7:

Ile Gln Val Gly Ala Lys Tyr Asp Ala Asn Asn Ile Ile Val Ala
 1               5                  10                  15

Ile Ala Tyr Gly Arg Thr Asn Tyr Lys Asp Ser Asn His Ser Tyr
                20                  25                  30

Thr Gln Lys Ile Pro Lys Ala Asn Ala Ala Asp Ala Asp Thr Asp
                35                  40                  45

Thr
 46

-continued

```
(2) INFORMATION FOR SEQ ID NO:8:

(i) SEQUENCE CHARACTERISTICS:
          (A) LENGTH: 138 nucleotides
          (B) TYPE: nucleic acid
          (C) STRANDEDNESS: double-stranded
          (D) TOPOLOGY: linear (ii) ORIGINAL SOURCE:
          (A) ORGANISM: H. influenzae (iii) SEQUENCE DESCRIPTION: SEQ ID NO:8:

ATTCAAGTTG GTGCAAAATA TGATGCTAAC AACATTATTG TAGCTATTGC          50

TTACGGTCGT ACAAATTATA AAGACAGTAA TCATAGTTAT ACGCAAAAAA         100

TCCCCAAAGC CAACGCCGCC GACGCCGACA CCGACACC                      138
```